US00PP34052P2

(12) United States Plant Patent
Matsumoto

(10) Patent No.: US PP34,052 P2
(45) Date of Patent: Mar. 22, 2022

(54) ***EVOLVULUS* PLANT NAMED 'RMEVO28301'**

(50) Latin Name: *Evolvulus hybrida*
Varietal Denomination: RMEVO28301

(71) Applicant: Rika Matsumoto, Omihachiman (JP)

(72) Inventor: Rika Matsumoto, Omihachiman (JP)

(73) Assignee: WINGEN, LLC, Mustang Ridge, TX (US)

( * ) Notice: Subject to any disclaimer, the term of this patent is extended or adjusted under 35 U.S.C. 154(b) by 0 days.

(21) Appl. No.: 17/223,668

(22) Filed: Apr. 6, 2021

(51) Int. Cl.
*A01H 5/02* (2018.01)
*A01H 6/00* (2018.01)

(52) U.S. Cl.
USPC ..... Plt./263.1

(58) Field of Classification Search
USPC ..... Plt./263.1
CPC ..... A01H 5/02; A01H 6/00
See application file for complete search history.

*Primary Examiner* — Keith O. Robinson
(74) *Attorney, Agent, or Firm* — C. Anne Whealy

(57) ABSTRACT

A new and distinct cultivar of *Evolvulus* plant named 'RMEVO28301', characterized by its upright and uniformly mounded plant habit; vigorous growth habit; freely branching habit, dense and bushy appearance; freely flowering habit and long flowering period; large violet blue-colored flowers with white-colored centers; and good garden performance.

1 Drawing Sheet

Botanical designation: *Evolvulus hybrida.*
Cultivar denomination: 'RMEVO28301'.

CROSS-REFERENCED TO CLOSELY RELATED APPLICATIONS

Title: *Evolvulus* Plant Named 'REMVO28301'
Inventor/Applicant: Rika Matsumoto
Provisional application Ser. No.: 62/974,516
Filed: Dec. 3, 2019
Inventor/Applicant does not claim the benefit of this provisional U.S. Patent Application.

STATEMENT REGARDING PRIOR DISCLOSURES BY INVENTOR/APPLICANT & ASSIGNEE

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Evolvulus* plant, botanically known as *Evolvulus hybrida* and hereinafter referred to by the name 'RMEVO28301'.

The new *Evolvulus* plant is a product of a planned breeding program conducted by the Inventor in Higashiomi, Shiga, Japan. The objective of the breeding program is to create new vigorous and mounding *Evolvulus* plants with numerous attractive flowers and long flowering period.

The new *Evolvulus* plant originated from a cross-pollination on Jul. 17, 2015 of a proprietary seedling selection of *Evolvulus hybrida* identified as code designation 07E12-01, not patented, as the female, or seed, parent with an unnamed cultivated selection of *Evolvulus hybrida*, not patented, as the male, or pollen, parent. The new *Evolvulus* plant was discovered and selected as a single flowering plant from within the progeny of the stated cross-pollination in a controlled greenhouse environment in Higashiomi, Shiga, Japan on Aug. 22, 2016.

Asexual reproduction of the new *Evolvulus* plant by vegetative tip cuttings since Aug. 23, 2016 in a controlled greenhouse in Higashiomi, Shiga, Japan has shown that the unique features of this new *Evolvulus* plant are stable and reproduced true to type in successive generations of asexual reproduction.

SUMMARY OF THE INVENTION

The following traits have been repeatedly observed and are determined to be the unique characteristics of 'RMEVO28301'. These characteristics in combination distinguish 'RMEVO28301' as a new and distinct *Evolvulus* plant:

1. Upright and uniformly mounded plant habit.
2. Vigorous growth habit.
3. Freely branching habit, dense and bushy appearance.
4. Freely flowering habit and long flowering period.
5. Large violet blue-colored flowers with white-colored centers.
6. Good garden performance.

Plants of the new *Evolvulus* can be compared to plants of the female parent selection. In side-by-side comparisons, plants of the new *Evolvulus* differ primarily from plants of the female parent selection in the following characteristics:

1. Plants of the new *Evolvulus* have a mounding plant habit whereas plants of the female parent selection have a creeping plant habit.

2. Plants of the new *Evolvulus* flower earlier than plants of the female parent selection.

Plants of the new *Evolvulus* can be compared to plants of the male parent selection. In side-by-side comparisons, plants of the new *Evolvulus* differ primarily from plants of the male parent selection in flower size as plants of the new *Evolvulus* have larger flowers than plants of the male parent selection.

Plants of the new *Evolvulus* can be compared to plants of *Evolvulus hybrida* 'American Blue', not patented. In side-by-side comparisons, plants of the new *Evolvulus* differ primarily from plants of 'American Blue' in the following characteristics:

1. Plants of the new *Evolvulus* have a mounding plant habit whereas plants of 'American Blue' have a creeping and sprawling plant habit.
2. Plants of the new *Evolvulus* flower earlier than plants of 'American Blue'.

Plants of the new *Evolvulus* can also be compared to plants of *Evolvulus hybrida* 'USEVO1201', disclosed in U.S. Plant Pat. No. 24,447. In side-by-side comparisons, plants of the new Evolvulus differ primarily from plants of 'RMEVO28301' in growth habit as plants of the new *Evolvulus* are more vigorous than and not as compact as plants of 'RMEVO28301'.

BRIEF DESCRIPTION OF THE PHOTOGRAPH

The accompanying photograph illustrates the overall appearance of the new *Evolvulus* plant showing the colors as true as it is reasonably possible to obtain in colored reproductions of this type. The photograph is a side perspective view of a typical flowering plant of 'RMEVO28301' grown in a container. Plants used for the photograph were grown during the summer in 33-cm containers an outdoor nursery in Carleton, Mich. During the production of the plants, day temperatures averaged 26° C. and night temperatures averaged 20° C. Plants were pinched one time and were 15 weeks old when the photograph was taken.

DETAILED BOTANICAL DESCRIPTION

The following observations, measurements and values describe plants grown during the summer in 30-cm containers in an outdoor nursery in Carleton, Mich. During the production of the plants, day temperatures averaged 26° C. and night temperatures averaged 20° C. Plants were 18 weeks old when the description was taken. In the following description, color references are made to The Royal Horticultural Society Colour Chart, 2015 Edition, except where general terms of ordinary dictionary significance are used.

Botanical classification: *Evolvulus hybrida* 'RMEVO28301'.

Parentage:

*Female, or seed, parent*.—Proprietary seedling selection of *Evolvulus hybrida* identified as code name 07E12-01, not patented.

*Male, or pollen, parent*.—Unnamed cultivated selection of *Evolvulus hybrida*, not patented.

Propagation:

*Type*.—By terminal cuttings.

*Time to initiate roots, summer*.—About three days at temperatures ranging from 16° C. to 29° C.

*Time to initiate roots, winter*.—About four days at temperatures ranging from 16° C. to 21° C.

*Time to produce a rooted plant, summer*.—About 15 days at temperatures ranging from 16° C. to 29° C.

*Time to produce a rooted plant, winter*.—About 20 days at temperatures ranging from 16° C. to 21° C.

*Root description*.—Medium in thickness, fibrous; typically white in color; actual color of the roots is dependent on substrate composition, water quality, fertilizer type and formulation, substrate temperature and physiological age of roots.

*Rooting habit*.—Freely branching; medium density.

Plant description:

*Plant and growth habit*.—Upright, outwardly spreading and mounding plant habit; freely branching growth habit with lateral branches developing at potentially at every node; dense and bushy appearance; vigorous growth habit.

*Plant height*.—About 16 cm.

*Plant diameter*.—About 50 cm by 52 cm.

Lateral branch description:

*Length*.—About 21 cm.

*Diameter*.—About 2 mm to 2.5 mm.

*Internode length*.—About 1.25 cm.

*Strength*.—Strong, wiry and flexible.

*Aspect*.—Initially upright then falling outwardly and decumbent.

*Texture and luster*.—Densely pubescent; matte.

*Color*.—Close to 144A variably tinged with close to 197A.

Leaf description:

*Arrangement*.—Alternate; simple.

*Length*.—About 3.6 cm.

*Width*.—About 1.75 cm.

*Shape*.—Elliptical to slightly obovate.

*Apex*.—Obtuse, rounded.

*Base*.—Attenuate to obtuse.

*Margin*.—Entire; not undulate.

*Texture and luster, upper surface*.—Slightly pubescent; slightly glossy.

*Texture and luster, lower surface*.—Pubescent; matte.

*Venation pattern*.—Pinnate; arcuate.

*Color*.—Developing leaves, upper surface: Close to 146A. Developing leaves, lower surface: Close to 147B. Fully expanded leaves, upper surface: Close to 147A; venation, close to 146A. Fully expanded leaves, lower surface: Close to 147B; venation, close to 146B.

*Petiole*.—Length: About 7 mm. Diameter: About 2 mm. Texture and luster, upper and lower surfaces: Pubescent; matte. Color, upper surface: Close to 146A. Color, lower surface: Close to 146B.

Flower description:

*Flower arrangement and habit*.—Salverform rotate flowers; flowers terminal and axillary; freely flowering habit with typically ten to twelve flower buds and flowers per terminal; flowers face upright to slightly outwardly.

*Fragrance*.—None detected.

*Natural flowering season*.—Early flowering habit, plants of the new *Evolvulus* begin flowering about 40 days after planting; plants flower continuously from spring until frost in Michigan.

*Flower longevity*.—Individual flowers last about one to two days on the plant; flowers persistent, but typically abscise when dry.

*Flower diameter*.—About 2.3 cm.

*Flower length* (*height*).—About 1 cm.

*Flower throat diameter*.—About 4 mm.

*Flower buds*.—Length: About 1.25 cm. Diameter: About 4 mm. Shape: Obovate to obelliptic. Color: Petals, close to 94A; sepals, close to 146A.

*Corolla*.—Arrangement: Five fused petals arranged in a salverform shape with a slender tube. Petal lobe length (from throat): About 1.1 cm. Petal lobe width: About 1.1 cm. Petal shape: Obovate to spatulate. Petal apex: Rounded or emarginate. Petal margin: Erose, ragged or entire. Petal texture and luster, upper surface: Smooth, glabrous; velvety; slightly glossy. Petal texture and luster, lower surface: Smooth, glabrous; matte. Throat texture and luster: Smooth, glabrous; matte. Tube texture and luster: Slightly pubescent; slightly glossy. Color: Petal lobe, when opening, upper surface: Close to 96A. Petal lobe, when opening, lower surface: Close to 96C. Petal lobe, fully opened, upper surface: Close to 96B; central star pattern, close to NN155A; venation, close to 96B; color becoming closer to 96B to 96C with development. Petal lobe, fully opened, lower surface: Close to 96B to 96C; venation, close to 96B to 96C; color becoming closer to 96C to 96D with development. Throat: Close to NN155A; venation, close to NN155A. Tube: Close to NN155A; venation, close to NN155A.

*Calyx*.—Arrangement: Star-shaped calyx with five sepals fused towards the base and arranged in a single whorl. Sepal length: About 5.5 mm. Sepal width: About 1.5 mm. Sepal shape: Lanceolate. Sepal apex: Acuminate. Sepal margin: Entire. Sepal texture and luster, upper surface: Smooth, glabrous; slightly glossy. Sepal texture and luster, lower surface: Densely pubescent; slightly glossy. Color, upper surface: Close to 144A. Color, lower surface: Close to 146A.

*Peduncles*.—Length: About 2.5 cm. Diameter: About 1.5 mm. Angle: If terminal, upright to slightly outwardly; if axillary, about 45° from stem axis. Strength: Strong, wiry and flexible. Texture: Pubescent. Color: Close to 144A.

*Reproductive organs*.—Stamens: Quantity: About five per flower. Filament length: About 7.5 mm. Filament color: Close to NN155D. Anther shape: Lanceolate. Anther length: About 2 mm. Anther color: Close to NN155A. Pollen amount: None observed. Pistils: Quantity: One to five per flower. Pistil length: About 7 mm. Style length: About 5.5 mm. Style color: Close to NN155D. Stigma shape: Fine and thread-like, bi-parted. Stigma color: Close to NN155D. Ovary color: Close to 145C. Seeds and fruits: To date, seed nor fruit development has not been observed on plants of the new *Evolvulus*.

Garden performance: Plants of the new *Evolvulus* have been observed to have good garden performance and tolerate wind, rain and temperatures ranging from about −5° C. to about 40° C.

Pathogen & pest resistance: To date, plants of the new *Evolvulus* have not been observed to be resistant to pathogens and pests common to *Evolvulus* plants.

It is claimed:

1. A new and distinct *Evolvulus* plant named 'RMEVO28301' as illustrated and described.

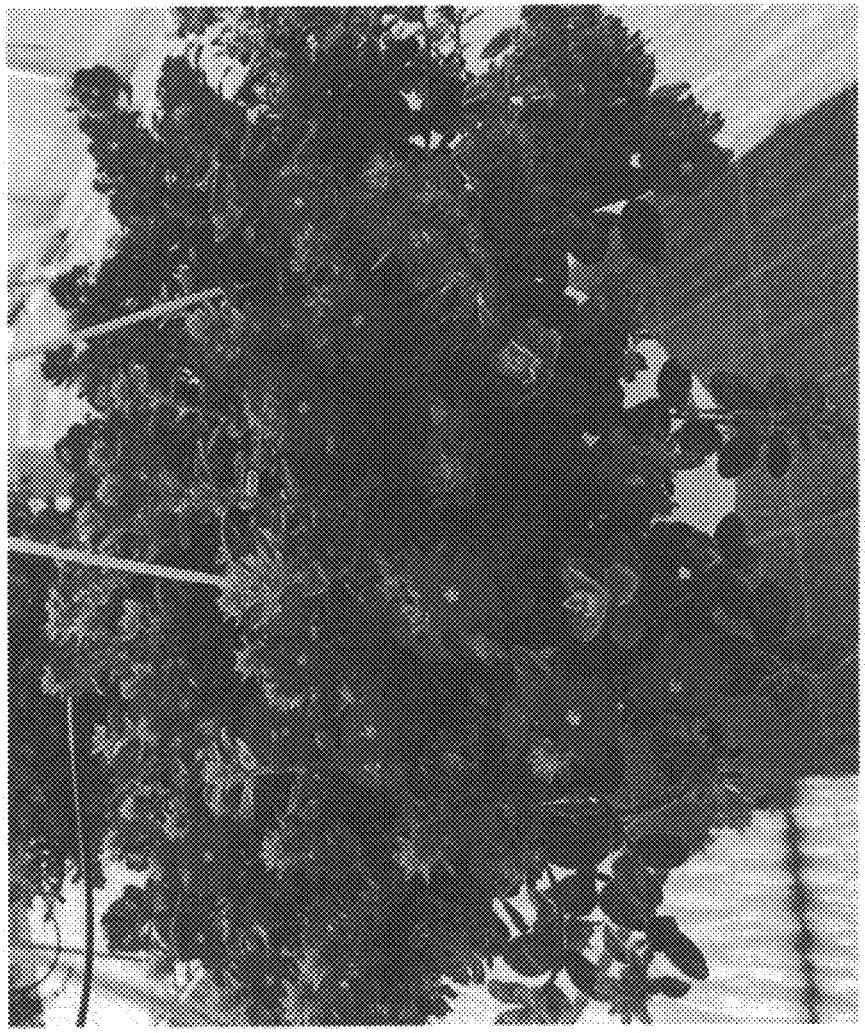

* * * * *